United States Patent
Ke et al.

(10) Patent No.: US 12,322,364 B1
(45) Date of Patent: Jun. 3, 2025

(54) NOISE REDUCTION GAS PATH STRUCTURE, GAS PATH DEVICE AND RESPIRATOR

(71) Applicant: SHENZHEN YAMIND MEDICAL TECHNOLOGY CO., LTD., Guangdong (CN)

(72) Inventors: Jun Ke, Guangdong (CN); Xu Li, Guangdong (CN); Shuiqi Zou, Guangdong (CN); Tao Wang, Guangdong (CN)

(73) Assignee: SHENZHEN YAMIND MEDICAL TECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 18/969,351

(22) Filed: Dec. 5, 2024

Related U.S. Application Data

(63) Continuation of application No. PCT/CN2024/121256, filed on Sep. 26, 2024.

(51) Int. Cl.
*G10K 11/162* (2006.01)
*A61M 16/00* (2006.01)
*G10K 11/172* (2006.01)

(52) U.S. Cl.
CPC ....... *G10K 11/162* (2013.01); *A61M 16/0003* (2014.02); *A61M 16/0066* (2013.01); *G10K 11/172* (2013.01); *A61M 2205/42* (2013.01)

(58) Field of Classification Search
CPC .......... A61M 16/0003; G10K 11/172; G10K 11/162
USPC .......................................... 181/212, 211, 224
See application file for complete search history.

(56) References Cited

U.S. PATENT DOCUMENTS

| | | | | |
|---|---|---|---|---|
| 6,790,012 | B2 * | 9/2004 | Sharp | F04B 39/066 |
| | | | | 417/313 |
| 7,350,496 | B2 * | 4/2008 | Nakayama | F02M 35/1283 |
| | | | | 123/184.57 |
| 7,717,230 | B2 * | 5/2010 | Takeuchi | F02M 35/1272 |
| | | | | 123/184.55 |
| 9,305,539 | B2 * | 4/2016 | Lind | F24F 7/04 |
| 10,928,096 | B2 * | 2/2021 | Hickey | F24F 13/24 |
| 11,141,552 | B2 * | 10/2021 | Librett | F04D 29/665 |
| 11,841,163 | B2 * | 12/2023 | Sugawara | F24F 13/02 |
| 11,869,470 | B2 * | 1/2024 | Hakuta | G10K 11/172 |

(Continued)

FOREIGN PATENT DOCUMENTS

| | | |
|---|---|---|
| CN | 116253293 A | 6/2023 |
| CN | 116421836 A | 7/2023 |
| WO | WO-2005097244 A1 * | 10/2005 ............ A61M 16/10 |

*Primary Examiner* — Forrest M Phillips
(74) *Attorney, Agent, or Firm* — Cooper Legal Group, LLC

(57) ABSTRACT

A noise reduction gas path structure includes a gas path chamber; an acoustically transparent and anti-aeration element in the gas path chamber, the acoustically transparent and anti-aeration element is configured to divide the gas path chamber into a gas flow portion and a sound-absorbing portion; and a sound-absorbing filler in the sound-absorbing portion, the sound-absorbing filler is configured to absorb sound entering the sound-absorbing portion from the gas flow portion through the acoustically transparent and anti-aeration element. A gas path device includes the above noise reduction gas path structure. And a respirator includes the gas path device.

8 Claims, 3 Drawing Sheets

(56) References Cited

U.S. PATENT DOCUMENTS

2014/0299406 A1\* 10/2014 Librett ............. A61M 16/0858
181/224

\* cited by examiner

NOISE REDUCTION GAS PATH STRUCTURE, GAS PATH DEVICE AND RESPIRATOR

CROSS-REFERENCE TO RELATED APPLICATION

This application is a continuation of PCT application serial no. PCT/CN2024/121256, filed on Sep. 26, 2024. The entirety of PCT application serial no. PCT/CN2024/121256 is hereby incorporated by reference herein and made a part of this specification.

TECHNICAL FIELD

The present application relates to the field of respirators, and more particularly, to a noise reduction gas path structure, a gas path device and a respirator.

BACKGROUND ART

The respirator, as a device with an artificial ventilation function, has been widely used in the treatment of respiratory failure, obstructive sleep apnea hypopnea syndrome and other diseases caused by various reasons. When using a respirator for treating respiratory diseases, there is often relatively high noise since the respirator needs to inhale gas from the outside for a series of gas treatment and then supplies it to the user for respiration, which affects the user's experience. The noise mainly comes from noise generated by gas flow and noise generated during operation of a fan. In order to eliminate the noise generated during the gas flow, some components related to noise reduction are correspondingly provided.

In the related art, as disclosed in Publication Number CN116421836A, entitled "Low-Noise Gas Source Box and Respirator", a low-noise respirator includes an upper cover, a turbine fan, an outlet hose, a sound-absorbing cotton and a lower cover, where a sound-absorbing chamber is formed by the upper cover and the lower cover, the turbine fan is disposed inside the sound-absorbing chamber, and an upper side and a lower side of an intake flow path are respectively provided with the sound-absorbing cotton. The sound-absorbing cotton is provided with back glue, an inner contour of the sound-absorbing cotton fits into a partition plate, and an outer contour thereof fits into an inner wall surface of the labyrinth of sound-absorbing chamber formed by the upper cover and the lower cover, and one side of the outer contour is configured with a groove for mounting an acoustic baffle, so as to achieve a better noise reduction effect on middle and high frequency noise.

In addition, for example, CN116253293A discloses an oxygen generator with noise reduction function, which is also provided with an element related to noise reduction. The implementation principle of Embodiment 2 thereof is that in the process of filtering vibration, a strut of a shock absorber moves up and down to swing a silencer board up and down, so as to form a gas flow, so that the silencer board may silence the exhaust gas discharged from the oxygen generator.

In the above related art, if noise reduction is performed by the sound-absorbing cotton, particulate matter is always precipitated and absorbed by a human body in use, which is harmful to the health of the human body. Moreover, if the noise reduction is performed by the silencer board, a certain spatial size is required to achieve the noise reduction, namely a certain small hole depth and a certain thickness of an internal air layer are required for the silencer board, which results in a rather large volume of the respirator.

SUMMARY

In order to miniaturize the volume of a respirator and make the inhaled gas healthy while achieving noise reduction, the present application provides a noise reduction gas path structure, a gas path device and a respirator.

In a first aspect, the noise reduction gas path structure provided in the present application adopts the following technical solution.

A noise reduction gas path structure includes:
a gas path chamber;
an acoustically transparent and anti-aeration element in the gas path chamber, the acoustically transparent and anti-aeration element is configured to divide the gas path chamber into a gas flow portion and a sound-absorbing portion; and
a sound-absorbing filler in the sound-absorbing portion, the sound-absorbing filler is configured to absorb sound entering the sound-absorbing portion from the gas flow portion through the acoustically transparent and anti-aeration element.

By adopting the above technical solution, sound in the gas may enter the sound-absorbing portion through the acoustically transparent and anti-aeration element and then be eliminated by the sound-absorbing filler in the sound-absorbing portion, but the gas does not enter the sound-absorbing portion, and therefore the sound-absorbing filler also does not precipitate particulate matter into the gas flow portion, so that the particulate matter in the gas may be eliminated while using the sound-absorbing filler, thereby miniaturizing the volume of the respirator and making the inhaled gas healthy while achieving noise reduction.

Optionally, the acoustically transparent and anti-aeration element is made of an elastic material to vibrate the acoustically transparent and anti-aeration element due to sound.

By adopting the above technical solution, when the sound passes through the acoustically transparent and anti-aeration element, the acoustically transparent and anti-aeration element would vibrate, so that energy in the sound is consumed by the vibration, thereby further improving the noise reduction capability.

Optionally, the sound-absorbing portion and the gas flow portion are configured to extend in parallel.

By adopting the above technical solution, a contact area between the gas flow and the acoustically transparent and anti-aeration element may be increased, so that more sound may enter the sound-absorbing portion, thereby improving the noise reduction capability.

Optionally, a resonance gap is formed between the sound-absorbing filler and the acoustically transparent and anti-aeration element.

By adopting the above technical solution, due to the resonance gap, a structure similar to a resonance cavity may be formed between the sound-absorbing filler and the acoustically transparent and anti-aeration element, thereby attenuating the noise.

In a second aspect, the present application provides a gas path device which adopts the following technical solution.

A gas path device includes the noise reduction gas path structure, a housing and a fan, where the noise reduction gas path structure is disposed in the housing, the housing is further provided with a power chamber in communication with the gas path chamber, and the fan is disposed in the power chamber.

By adopting the above technical solution, since the noise reduction gas path structure is applied in the gas path device, the gas path device may have a smaller volume while achieving noise reduction, and the gas sent out by the gas path device also does not contain particulate matter, so that the gas inhaled by people is healthy. In addition, the power chamber is formed, so that the gas does not enter the fan immediately after leaving the gas path chamber, but firstly accumulates in the power chamber gradually and then enters the fan, so that a flow rate does not change significantly, thereby reducing the generation of additional noise.

Optionally, the gas path chamber is configured to extend in a serpentine manner.

Compared with the straight extension of the gas path chamber, on the one hand, with the present design, a more compact structure of the gas path device without a too long side of the gas path device in a certain direction may be obtained, thereby facilitating the miniaturization of the respirator. On the other hand, the gas flows slower at the bend than at a straight line, more sound may pass through the acoustically transparent and anti-aeration element to enter the sound-absorbing portion at the bend, thereby facilitating the improvement of the noise reduction capability.

Optionally, the gas path chamber is provided with a guide plate at a bend, and the guide plate is configured to bend corresponding to the bend of the gas path chamber.

Since the gas flow is more strongly collided with an inner wall of the gas flow portion at the bend than at the straight line, the guide plate is provided to reduce the generation of new noise while increasing a contact area between the gas flow and acoustically transparent and anti-aeration element, thereby facilitating the improvement of the noise reduction capability.

Optionally, the gas path device is so configured, that the gas flow passes through the gas path chamber and the power chamber sequentially, the power chamber is positioned above the gas path chamber, and the gas path chamber extends in a zigzag manner in a horizontal direction.

By adopting the above technical solution, the gas path chamber is saturated with the gas at a low flow velocity, while the power chamber is unsaturated with the gas at a high flow velocity, so that a pressure difference of the gas at the connection position between the gas path chamber and the power chamber is not too large, thereby reducing the noise at the connection position between the gas path chamber and the power chamber. In addition, the housing may be provided with a flap at the power chamber, so as to facilitate the maintenance of the fan.

Optionally, the housing is divided into an upper hood body and a lower plate, the upper hood body has the power chamber, a lower side of the upper hood body is configured with a gas flow slot, a slot opening of the gas flow slot is covered by the acoustically transparent and anti-aeration element to form the gas flow portion, the lower plate is positioned on a side of the acoustically transparent and anti-aeration element away from the upper hood body, the sound-absorbing portion is formed by the lower plate and the acoustically transparent and anti-aeration element, and the acoustically transparent and anti-aeration element is clamped and fixed by the lower plate and the upper hood body.

By adopting the above technical solution, the acoustically transparent and anti-aeration element is clamped by the lower plate and the upper hood body to divide the gas path chamber into the gas flow portion and the sound-absorbing portion, namely the upper hood body, the acoustically transparent and anti-aeration element and the lower plate are sequentially disposed from top to bottom, and therefore the upper hood body is separated from the lower plate directly by the acoustically transparent and anti-aeration element in structural distribution, so as to obtain a better sealing through separation between the gas flow portion and the sound-absorbing portion. Secondly, the acoustically transparent and anti-aeration element is clamped and fixed by the upper hood body and the lower plate, such that the acoustically transparent and anti-aeration element would be compressed to deform, so as to obtain a better connection tightness between the acoustically transparent and anti-aeration element and the upper hood body and the lower plate more likely while obtaining a better convenience for assembling and disassembling the acoustically transparent and anti-aeration element, the upper hood body and the lower plate. Thirdly, the vibration generated during the operation of the fan is firstly attenuated by passing through the acoustically transparent and anti-aeration element and then transmitted to the lower plate, thereby reducing the vibration amplitude of the whole gas path device, and thus further reducing the noise generated by the gas path device.

In a third aspect, the respirator provided in the present application adopts the following technical solution.

A respirator includes the gas path device.

By adopting the above technical solution, a volume of the respirator may be miniaturized and an inhaled gas may be kept healthy while achieving noise reduction.

In summary, the present application includes at least one of the following beneficial technical effects.

1. With regard to the noise reduction gas path structure, sound in the gas may enter the sound-absorbing portion through the acoustically transparent and anti-aeration element and then be eliminated by the sound-absorbing filler in the sound-absorbing portion, but the gas does not enter the sound-absorbing portion, and therefore the sound-absorbing filler also does not precipitate particulate matter into the gas flow portion, so that the particulate matter in the gas may be eliminated while using the sound-absorbing filler, thereby miniaturizing the volume of the respirator and making the inhaled gas healthy while achieving noise reduction.

2. With regard to the gas path device, the acoustically transparent and anti-aeration element is clamped by the lower plate and the upper hood body to divide the gas path chamber into the gas flow portion and the sound-absorbing portion, so as to obtain a better sealing through separation between the gas flow portion and the sound-absorbing portion while obtaining a better convenience for assembling and disassembling the acoustically transparent and anti-aeration element. Additionally, the vibration generated during the operation of the fan is firstly attenuated by passing through the acoustically transparent and anti-aeration element and then transmitted to the lower plate, thereby reducing the vibration amplitude of the whole gas path device, and thus further reducing the noise generated by the gas path device.

DETAILED DESCRIPTION

The present application is described in further detail below with reference to FIG. 1 to FIG. 3.

An embodiment of the present application discloses a noise reduction gas path structure.

Figure 1:
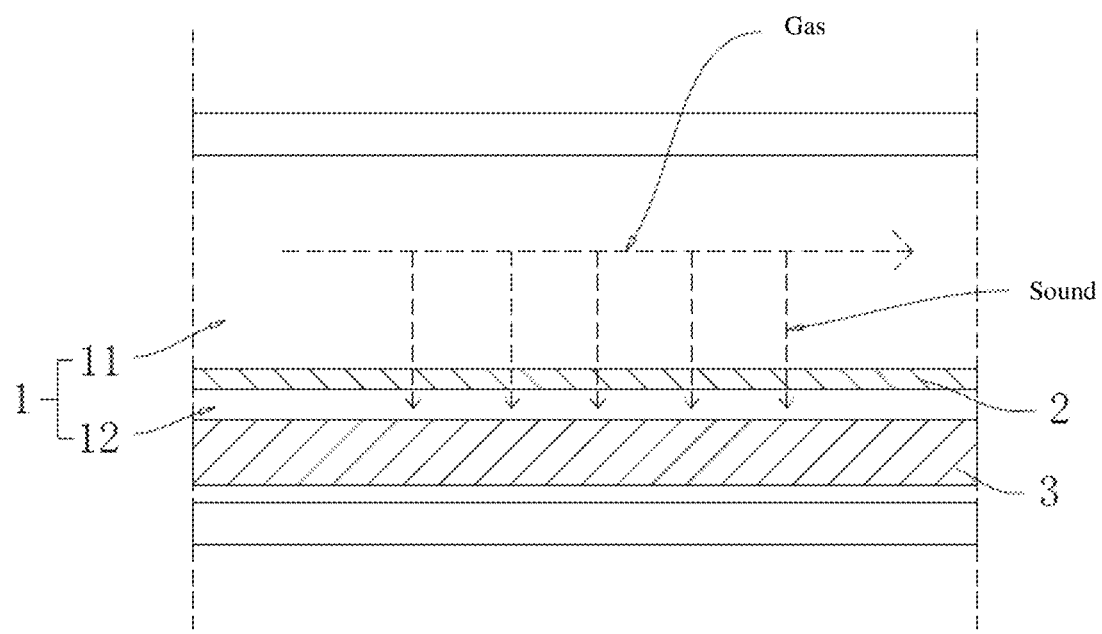
FIG. 1 is a schematic view showing the structure of a noise reduction gas path structure in an embodiment of the present application.

Referring to FIG. 1, the noise reduction gas path structure includes a gas path chamber 1, an acoustically transparent and anti-aeration element 2 as well as a sound-absorbing filler 3. The gas path chamber 1 is configured to be a passage having at least two connection holes. The acoustically transparent and anti-aeration element 2 is disposed in the gas path chamber 1, the gas path chamber 1 is divided into a gas flow portion 11 and a sound-absorbing portion 12 by the acoustically transparent and anti-aeration element 2, a gas cannot flow between the gas flow portion 11 and the sound-absorbing portion 12, but sound may propagate between the gas flow portion 11 and the sound-absorbing portion 12. The sound-absorbing filler 3 is disposed in the sound-absorbing portion 12, and a material of the sound-absorbing filler 3 includes, but is not limited to, sound-absorbing cotton, polyurethane foam plastic, wave crest sponge, polystyrene foam and a fiber material. The sound-absorbing filler 3 may absorb the sound entering the sound-absorbing portion 12 from the gas flow portion 11 through the acoustically transparent and anti-aeration element 2.

Referring to FIG. 1, the operation principle is as follows: sound in the gas may enter the sound-absorbing portion 12 through the acoustically transparent and anti-aeration element 2 and then be eliminated by the sound-absorbing filler 3 in the sound-absorbing portion 12, but the gas does not enter the sound-absorbing portion 12, and therefore the sound-absorbing filler 3 also does not precipitate particulate matter into the gas flow portion 11. So the particulate matter in the gas may be eliminated while using the sound-absorbing filler 3, thereby miniaturizing the volume of the respirator and making the inhaled gas healthy while achieving noise reduction.

Referring to FIG. 1, the parameter of the acoustically transparent and anti-aeration element 2, which is mainly considered when selecting the material, is the acoustical permeability. Based on the acoustical permeability, the acoustically transparent and anti-aeration element 2 may be made of a hard material, and may also be made of a soft material, where the hard material includes, but is not limited to, carbon fiber and glass fiber, and the soft material includes, but is not limited to, rubber, polyethylene and TPU. In this embodiment, in order to further improve the noise reduction capability, the acoustically transparent and anti-aeration element 2 is optionally made of a soft material, such that the acoustically transparent and anti-aeration element 2 vibrates when the sound passes through the acoustically transparent and anti-aeration element 2, and therefore energy in the sound may be consumed in virtue of the vibration, thereby achieving the purpose of improving the noise reduction capability.

Referring to FIG. 1, in order to that more sound enters the sound-absorbing portion 12, the sound-absorbing portion 12 and the gas flow portion 11 extend in parallel, and specifically, the sound-absorbing portion 12 and the gas flow portion 11 extend in the same shape. Viewed from a cross section of the gas path chamber 1, the gas flow portion 11 and the sound-absorbing portion 12 are of separate multi-layer structures, so that in a process of gradual forward movement of the gas flow, the sound may continuously enter the sound-absorbing portion 12 through the acoustically transparent and anti-aeration element 2, thereby improving the noise reduction capability.

Referring to FIG. 1, in order to maintain the vibration of the acoustically transparent and anti-aeration element 2 while further reducing noise, a resonance gap is formed between the sound-absorbing filler 3 and the acoustically transparent and anti-aeration element 2, so that a structure similar to a resonance cavity is also formed between the sound-absorbing filler 3 and the acoustically transparent and anti-aeration element 2 while achieving the vibration of the acoustically transparent and anti-aeration element 2, thereby further eliminating noise.

The implementation principle of the noise reduction gas path structure in the present embodiment is as follows: sound in the gas may enter the sound-absorbing portion 12 through the acoustically transparent and anti-aeration element 2 and then be eliminated by the sound-absorbing filler 3 in the sound-absorbing portion 12, but the gas does not enter the sound-absorbing portion 12, and therefore the sound-absorbing filler 3 also does not precipitate particulate matter into the gas flow portion 11, so that the particulate matter in the gas may be eliminated while using the sound-absorbing filler 3, thereby miniaturizing the volume of the respirator and making the inhaled gas healthy while achieving noise reduction.

An embodiment of the present application further discloses a gas path device.

Figure 2:
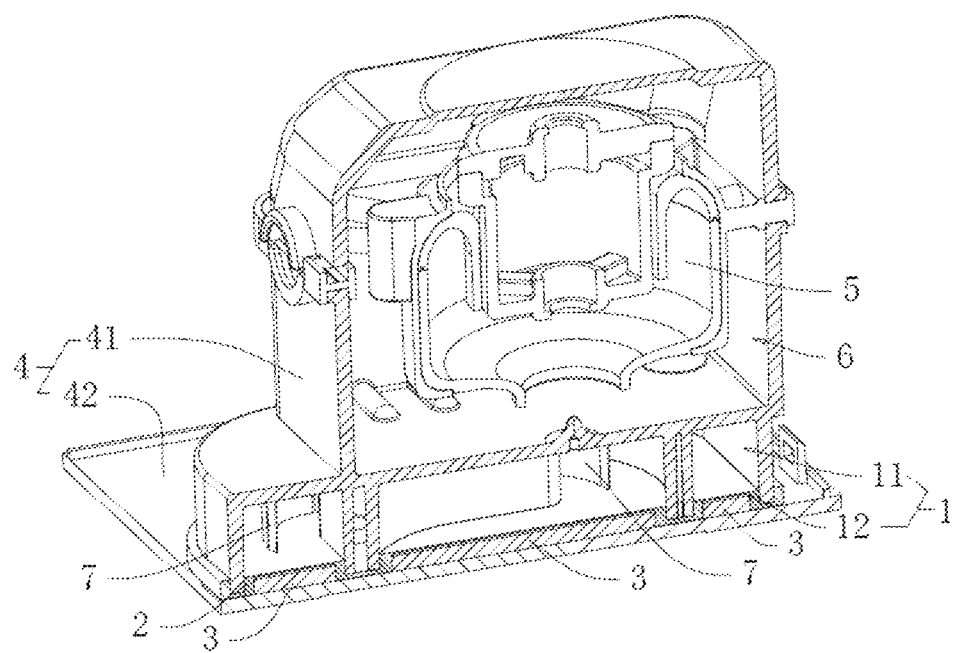
FIG. 2 is a sectional view showing the structure of a gas path device in an embodiment of the present application.
Figure 3:
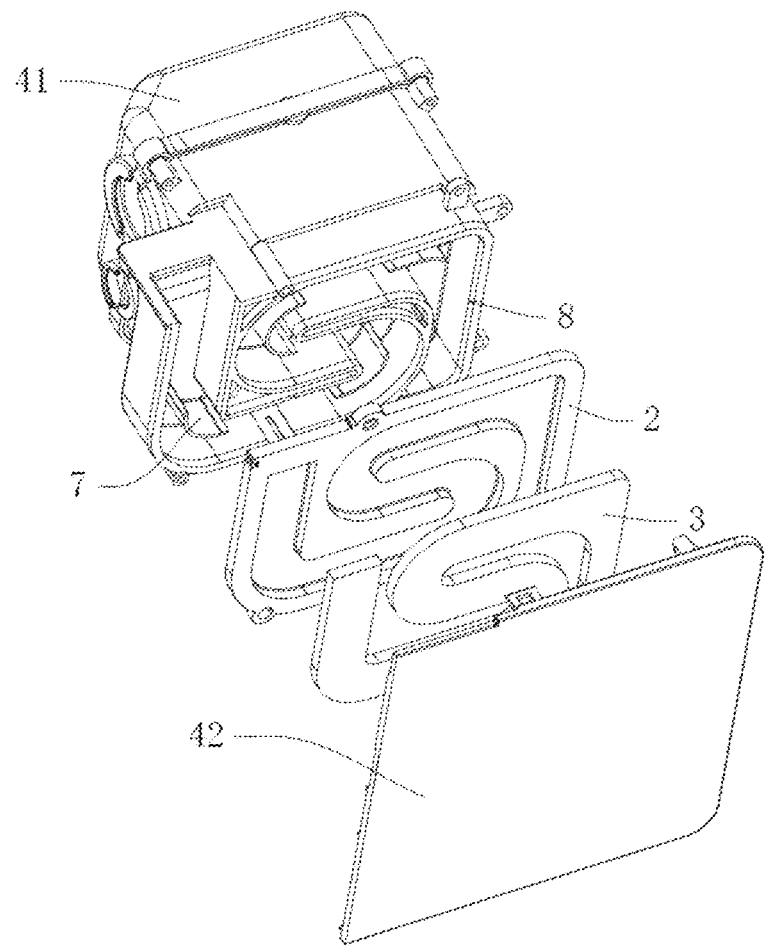
FIG. 3 is a schematic diagram illustrating the connection mode among an upper hood body, a lower plate and an acoustically transparent and anti-aeration element in an embodiment of the present application.

Referring to FIG. 2 and FIG. 3, the gas path device includes the above noise reduction gas path structure, a housing 4 and a fan 5, where the noise reduction gas path structure is disposed in the housing 4, so that the housing 4 has a gas path chamber 1. Additionally, the housing further has a power chamber 6 in communication with the gas path chamber 1, and the fan 5 is disposed in the power chamber 6. The gas path device may make the supplied gas healthy and miniaturize the volume of the gas path device itself while achieving noise reduction by virtue of the advantages of the noise reduction gas path structure. In addition, the power chamber 6 is formed, so that the gas does not enter the fan 5 immediately after leaving the gas path chamber 1, but accumulates in the power chamber 6 gradually and then enters the fan 5, so that a flow rate does not change significantly, thereby reducing the generation of additional noise.

Referring to FIG. 2 and FIG. 3, in order to improve the noise reduction capability, firstly, the gas path chamber 1 is configured to extend in a serpentine manner, and a flow velocity of the gas flow at a bend is lower than that at a straight line, so that more sound may enter the sound-absorbing portion 12 through the acoustically transparent and anti-aeration element 2 at the bend to promote the noise reduction capability. In addition, the gas path would not extend too long in a certain direction based on the extension manner of the gas path chamber 1, thereby promoting the miniaturization of the respirator.

Referring to FIG. 2 and FIG. 3, secondly, the gas path chamber 1 is integrally formed with a guide plate 7 at the bend, and the guide plate 7 extends in a shape corresponding to a bending shape of the gas path chamber 1 at the bend, so that the gas flow may be better guided to turn around when passing through the bend, so as to attenuate the collision between the gas flow and an inner wall of the gas flow portion 11 at the bend, thereby reducing the generation of new noise, and thus improving the noise reduction capability.

Referring to FIG. 2 and FIG. 3, furthermore, the gas flow passes through the gas path chamber 1 and the power chamber 6 sequentially, and in the operation process, the gas slowly accumulates in the gas path chamber 1 while the gas in the power chamber 6 is small in amount and rapidly diffuses since the gas path chamber 1 extends in a zigzag way in a horizontal direction and the power chamber 6 is positioned above the gas path chamber 1, so that the gas path chamber 1 is saturated with the gas at a low flow velocity, while the power chamber 6 is unsaturated with the gas at a high flow velocity, therefore, a pressure difference of the gas at a connection position between the gas path chamber 1 and the power chamber 6 is not too large, and therefore the noise at the connection position between the gas path chamber 1 and the power chamber 6 may be reduced.

Referring to FIG. 2 and FIG. 3, in the present embodiment, since the gas path chamber 1 is configured to extend in a serpentine manner in the horizontal direction, only one acoustically transparent and anti-aeration element 2 is disposed horizontally with the gas flow portion 11 positioned above it and the sound-absorbing portion 12 positioned below it, to achieve the miniaturization of the gas path device. Based on this structural form, in order to facilitate the mounting of the acoustically transparent and anti-aeration element 2 and the separation of the gas flow portion 11 from the sound-absorbing portion 12 by the acoustically transparent and anti-aeration element 2 with higher sealing property, it is designed correspondingly that the housing 4 is divided into an upper hood body 41 and a lower plate 42, where the upper hood body 41 has the above-mentioned power chamber 6, a lower side of the upper hood body 41 is configured with a gas flow slot 8, and a slot opening of the gas flow slot 8 is covered by the acoustically transparent and anti-aeration element 2 to form the above-mentioned gas flow portion 11. The lower plate 42 is positioned on a side of the acoustically transparent and anti-aeration element 2 away from the upper hood body 41, the above-mentioned sound-absorbing portion 12 is formed between the lower plate 42 and a surface of the side of the acoustically transparent and anti-aeration element 2 away from the upper hood body 41. In addition, the acoustically transparent and anti-aeration element 2 is clamped and fixed by the lower plate 42 and the upper hood body 41, such that the acoustically transparent and anti-aeration element 2 may be compressed to deform.

Referring to FIG. 2 and FIG. 3, the matching configuration among the acoustically transparent and anti-aeration element 2, the upper hood body 41 and the lower plate 42 has the following advantages: firstly, the upper hood body 41, the acoustically transparent and anti-aeration element 2 and the lower plate 42 are sequentially arranged from top to bottom, such that the upper hood body 41 is separated from the lower plate 42 directly by the acoustically transparent and anti-aeration element 2 in the structural distribution, so as to obtain a better sealing through separation between the gas flow portion 11 and the sound-absorbing portion 12. Secondly, the acoustically transparent and anti-aeration element 2 is clamped and fixed by the upper hood body 41 and the lower plate 42, such that the acoustically transparent and anti-aeration element 2 would be compressed to deform, so as to obtain a better connection tightness between the acoustically transparent and anti-aeration element 2 and the upper hood body 41 and the lower plate 42 more likely while obtaining a better convenience for assembling and disassembling the acoustically transparent and anti-aeration element 2, the upper hood body 41 and the lower plate 42. Thirdly, since the acoustically transparent and anti-aeration element 2 is made of an elastic material, the vibration generated during the operation of the fan 5 is firstly attenuated by passing through the acoustically transparent and anti-aeration element 2 and then transmitted to the lower plate 42, thereby reducing the vibration amplitude of the whole gas path device, and thus further reducing the noise generated by the gas path device.

The implementation principle of the gas path device according to the present embodiment is as follows: firstly, the gas path device may be miniaturized and the supplied gas healthy may be obtained while achieving noise reduction by virtue of the noise reduction gas path structure; and secondly, the acoustically transparent and anti-aeration element 2 made of the elastic material is clamped and fixed by virtue of the upper hood body 41 and the lower plate 42, so that the vibration generated during the operation of the fan 5 is attenuated and then transmitted to the lower plate 42, the vibration amplitude of the whole gas path device is smaller, thereby improving the noise reduction capability of the gas path device by eliminating other noise.

An embodiment of the present application further discloses a respirator. The respirator includes the above gas path device, where the lower plate 42 in the gas path device is a part of a shell structure of the respirator, so that the respirator may attenuate noise generated by air flow, and may also attenuate noise generated by vibration of the fan 5, thereby miniaturizing a volume of the respirator and making a gas inhaled by people healthy while achieving noise reduction.

The foregoing is all optional embodiments of the present application and does not limit the scope of protection of the present application on this basis, and therefore any equivalent change made based on a structure, shape and principle of the present application shall fall within the scope of protection of the present application.

LIST OF REFERENCE SIGNS 1 gas path chamber
11 gas flow portion
12 sound-absorbing portion
2 acoustically transparent and anti-aeration element
3 sound-absorbing filler
4 housing
41 upper hood body
42 lower plate
5 fan
6 power chamber
7 guide plate
8 gas flow slot

What is claimed is:
1. A noise reduction gas path structure, comprising:
a gas path chamber;
an acoustically transparent and anti-aeration element in the gas path chamber, wherein the acoustically transparent and anti-aeration element is configured to divide the gas path chamber into a gas flow portion and a sound-absorbing portion; and
a sound-absorbing filler in the sound-absorbing portion, the sound-absorbing filler is configured to absorb sound entering the sound-absorbing portion from the gas flow portion through the acoustically transparent and anti-aeration element,
wherein the acoustically transparent and anti-aeration element is made of an elastic material to vibrate the acoustically transparent and anti-aeration element due to the sound, and wherein a resonance gap is formed between the sound-absorbing filler and the acoustically transparent and anti-aeration element.

2. The noise reduction gas path structure according to claim 1, wherein the sound-absorbing portion and the gas flow portion are configured to extend in parallel.

3. A gas path device, comprising the noise reduction gas path structure according to claim 1, a housing and a fan, wherein the noise reduction gas path structure is disposed in the housing, the housing is further provided with a power chamber in communication with the gas path chamber, and the fan is disposed in the power chamber.

4. The gas path device according to claim 3, wherein the gas path chamber is configured to extend in a serpentine manner.

5. The gas path device according to claim 4, wherein the gas path chamber is provided with a guide plate at a bend of the gas path chamber, and the guide plate is configured to bend corresponding to the bend of the gas path chamber.

6. The gas path device according to claim 4, wherein the gas path device is configured such that a gas flow passes through the gas path chamber and the power chamber sequentially, the power chamber is positioned above the gas path chamber, and the gas path chamber extends in a zigzag manner in a horizontal direction.

7. The gas path device according to claim 6, wherein the housing is divided into an upper hood body and a lower plate, the upper hood body has the power chamber, a lower side of the upper hood body is configured with a gas flow slot, a slot opening of the gas flow slot is covered by the acoustically transparent and anti-aeration element to form the gas flow portion, the lower plate is positioned on a side of the acoustically transparent and anti-aeration element away from the upper hood body, the sound-absorbing portion is formed by the lower plate and the acoustically transparent and anti-aeration element, and the acoustically transparent and anti-aeration element is clamped and fixed by the lower plate and the upper hood body.

8. A respirator, comprising the gas path device according to claim 3.

* * * * *